(12) United States Patent
Nagahama et al.

(10) Patent No.: US 9,683,090 B2
(45) Date of Patent: Jun. 20, 2017

(54) POLYESTER RESIN COMPOSITION CONTAINING AMINO-TRIAZINE DERIVATIVE

(71) Applicant: NISSAN CHEMICAL INDUSTRIES, LTD., Tokyo (JP)

(72) Inventors: Takuma Nagahama, Funabashi (JP); Takeshi Suwa, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/778,288

(22) PCT Filed: Mar. 19, 2014

(86) PCT No.: PCT/JP2014/057549
§ 371 (c)(1),
(2) Date: Sep. 18, 2015

(87) PCT Pub. No.: WO2014/148555
PCT Pub. Date: Sep. 25, 2014

(65) Prior Publication Data
US 2016/0194477 A1    Jul. 7, 2016

(30) Foreign Application Priority Data

Mar. 22, 2013  (JP) .................. 2013-060129

(51) Int. Cl.
*C08K 5/3492* (2006.01)
*C08L 67/00* (2006.01)
(Continued)

(52) U.S. Cl.
CPC ........ *C08K 5/34922* (2013.01); *C07D 251/70* (2013.01); *C08K 5/0083* (2013.01); *C08L 67/00* (2013.01)

(58) Field of Classification Search
CPC  C08K 5/34922; C08K 5/0083; C07D 251/70; C08L 67/00
See application file for complete search history.

(56) References Cited

U.S. PATENT DOCUMENTS

| 3,101,335 A | 8/1963 | Scott et al. |
| 3,793,289 A * | 2/1974 | Koch .................. C08K 5/3492 524/100 |
| 2005/0272839 A1* | 12/2005 | Bauer .................. C08K 5/5313 524/115 |

FOREIGN PATENT DOCUMENTS

JP    S53-81562 A    7/1978
JP    H07-2804 A     1/1995
(Continued)

OTHER PUBLICATIONS

JP 2005256809 A, Sep. 2005, DERWENT Ab.*
(Continued)

*Primary Examiner* — Satya Sastri
(74) *Attorney, Agent, or Firm* — Oliff PLC

(57) ABSTRACT

A polyester resin composition containing 100 parts by mass of a polyester resin and 0.01 to 10 parts by mass of a 2-amino-1,3,5-triazine derivative of Formula [1]:

(Continued)

a polyester resin molded body obtained by the composition, and a crystal nucleating agent including the triazine derivative. A polyester resin composition containing a crystal nucleating agent that makes it possible to produce, with high productivity, a polyester resin molded product that promotes polyester resin crystallization and maintains high transparency after crystallization and is applicable for a wide variety of uses can be provided.

7 Claims, 1 Drawing Sheet

(51) Int. Cl.
  *C07D 251/70* (2006.01)
  *C08K 5/00* (2006.01)

(56) References Cited

FOREIGN PATENT DOCUMENTS

| JP | H08-3432 A | 1/1996 |
| JP | H09-20761 A | 1/1997 |
| JP | H10-87975 A | 4/1998 |
| JP | H10-158369 A | 6/1998 |
| JP | 2000-273792 A | 10/2000 |
| JP | 2003-192883 A | 7/2003 |
| JP | 2005256809 A * | 9/2005 |
| JP | 2011-006654 A | 1/2011 |
| JP | 2012-067218 A | 4/2012 |
| JP | 2013-018912 A | 1/2013 |
| WO | 00/27829 A1 | 5/2000 |
| WO | 2005/097894 A1 | 10/2005 |

OTHER PUBLICATIONS https://en.wikipedia.org/wiki/Acyl, May 2004.*
Oshima, Yoshibumi et al., "Studies on Melamine Derivatives Part II," Journal of Synthetic Organic Chemistry, vol. 15, No. 9, pp. 471-473, (1957).
Oshima, Yoshibumi et al., "Studies on Melamine Derivatives. V," Journal of Synthetic Organic Chemistry, vol. 19, No. 10, pp. 704-710, (1961).
Kitajima, Hidehiko et al., "Acylation of Melamine by Substituted Benzoyl Chlorides," Journal of Synthetic Organic Chemistry, vol. 30, No. 4, pp. 379-385, (1972).
Cason, James, "The Nitration of Melamine and of Triacetylmelamine," Journal of the American Chemical Society, vol. 69, Issue 3, pp. 495-498, (1947).
Translation of Jun. 24, 2014 Written Opinion issued in International Patent Application No. PCT/JP2014/057549.
Jun. 24, 2014 Search Report issued in International Patent Application No. PCT/JP2014/057549.

* cited by examiner

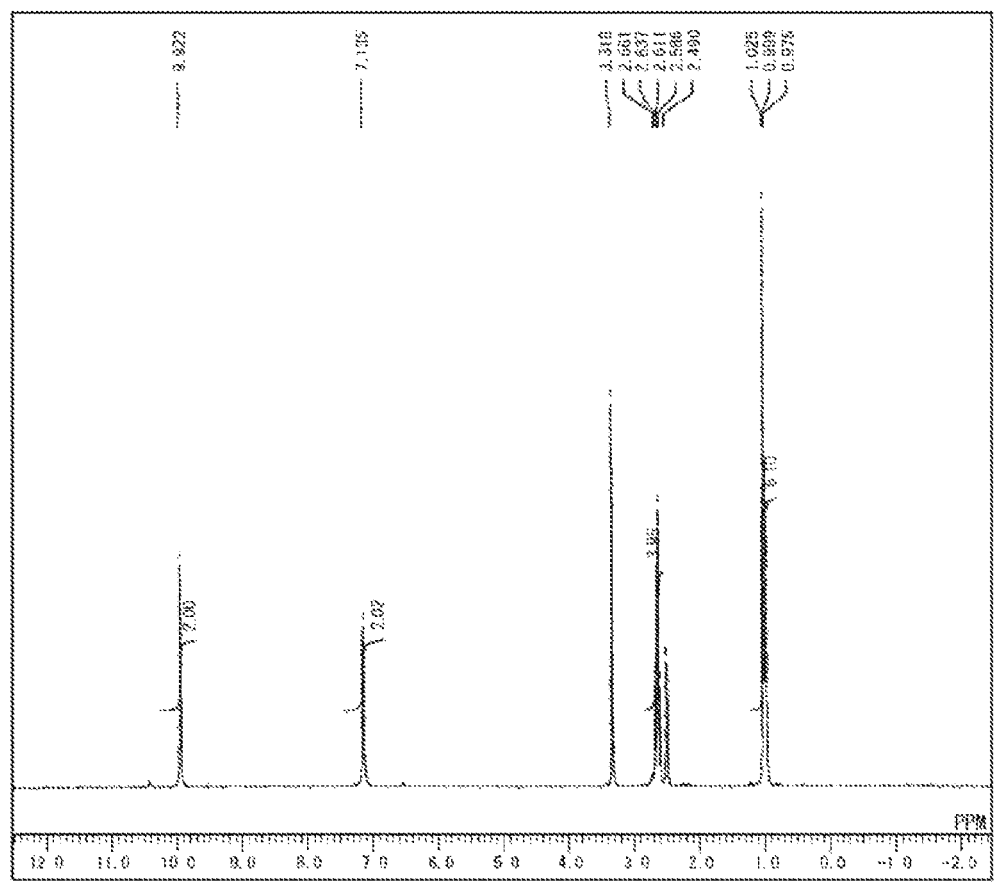

POLYESTER RESIN COMPOSITION CONTAINING AMINO-TRIAZINE DERIVATIVE

TECHNICAL FIELD

The present invention relates to a polyester resin composition, and in particular, a polyester resin composition containing an amino-triazine derivative.

BACKGROUND ART

A polyester resin has been widely used in industry for fibers and films since the polyester resin has excellent heat resistance, chemical resistance, mechanical properties, and electrical properties, and excellent cost/performance. In recent years, a biodegradable aliphatic polyester in the natural environment has been vigorously researched from the viewpoints of protection of the natural environment. In particular, a poly(lactic acid) resin is expected, for example, for packing materials such as a container and a film, fiber materials such as clothes, a floor mat, and an interior material for vehicles, and molding materials such as a housing and a part of electrical and electronic products since the poly(lactic acid) resin has a melting point as high as 160 to 180° C. and excellent transparency.

However, the polyester resin including the polylactic acid) resin has a disadvantage in which a molded product produced by injection molding or the like particularly without drawing is likely to have lower crystallinity and be softened at a temperature exceeding a glass transition temperature of about 60° C. This is because the polyester resin generally has an extremely low crystallization rate although it is a crystalline resin. In order to increase the crystallinity, a method of increasing the temperature of a mold during injection molding to extend the cooling time in the mold has been attempted. However, the method has a problem of productivity since a molding cycle is extended. In order to produce a polyester resin molded product with high productivity and use the molded product for a wide variety of applications, an increase in the crystallization rate and the crystallinity and an improvement in molding processability and heat resistance have been attempted.

As a method of improving the crystallization rate of a polyester resin, a method of adding a crystal nucleating agent has been generally known. The crystal nucleating agent acts as a primary crystal nucleator of a crystalline polymer to promote crystal growth, and serves to make the crystallite size fine and increase the crystallization rate. As a crystal nucleating agent of a polyester resin, metal salts of organic acids such as potassium benzoate and magnesium stearate and inorganic compounds such as talc, silica, and calcium sulfate have been conventionally proposed. As a crystal nucleating agent of a polylactic acid) resin, inorganic particles including talc or boron nitride that has a particle diameter equal to or less than a specific particle diameter (Patent Document 1), an amide compound of a specific formula (Patent Documents 2 and 3), a sorbitol derivative of a specific formula (Patent Document 4), a phosphoric acid ester metal salt of a specific formula (Patent Document 5), and the like have been disclosed. It has been disclosed that a metal salt of specific phosphonic acid compound, specifically zinc phenylphosphonate exhibits excellent performance (Patent Document 6).

PRIOR ART DOCUMENTS

Patent Documents

Patent Document 1: Japanese Patent Application Publication No. H8-3432 (JP H8-3432 A)
Patent Document 2: Japanese Patent Application Publication No. H10-87975 (JP H10-87975 A)
Patent Document 3: Japanese Patent Application Publication No. 2011-6654 (JP 2011-6654 A)
Patent Document 4: Japanese Patent Application Publication No. H10-158369 (JP H10-158369 A)
Patent Document 5: Japanese Patent Application Publication No, 2003-192883 (JP 2003-192883 A)
Patent Document 6: International Publication WO 2005/097894

SUMMARY OF THE INVENTION

Problem to be Solved by the Invention

As described above, various crystal nucleating agents for increasing the crystallization rate and crystallinity of a polyester resin have been proposed. In recent years, it is desired to develop a more effective crystal nucleating agent that achieves higher molding processability and heat resistance of the polyester resin.

In a polyester resin composition containing a crystal nucleating agent conventionally proposed, there is a case in which the transparency of a polyester resin is deteriorated by crystallization. Therefore, it is desired to provide a resin molded body having high transparency even after crystallization.

It is an object of the present invention to provide a polyester resin composition containing a crystal nucleating agent that makes it possible to produce, with high productivity, a polyester resin molded product that promotes polyester resin crystallization and maintains high transparency after crystallization and is applicable for a wide variety of uses.

Means for Solving the Problems

In order to solve the above-described problems, the present inventors have intensively investigated, and as a result, found that a specific 2-amino-1,3,5-triazine derivative can enhance the crystallization rate of a polyester resin and achieve a molded body having excellent transparency, in particular, after crystallization. Thus, the present invention has been accomplished.

Specifically, as a first aspect, the present invention relates to a polyester resin composition containing 100 parts by mass of polyester resin and 0.01 to 10 parts by mass of 2-amino-1,3,5-triazine derivative of Formula [1]:

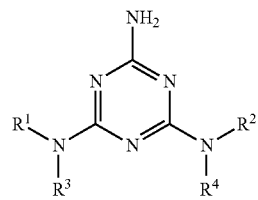

[1]

(wherein each of $R^1$ and $R^2$ is independently —C(=O)$R^5$, —C(=O)O$R^6$, —C(=O)N$R^7R^8$, or —SO$_2R^9$, and each of $R^3$ and $R^4$ is independently a hydrogen atom, a $C_{1-6}$ alkyl group, —C(=O)$R^5$, —C(=O)N$R^7R^8$, or —SO$_2R^9$, wherein each of $R^5$, $R^6$, and $R^9$ is independently a $C_{1-20}$ alkyl group or a phenyl group optionally substituted with a $C_{1-6}$ alkyl group, and each of $R^7$ and $R^8$ is independently a hydrogen atom, a $C_{1-20}$ alkyl group, or a phenyl group optionally substituted with a $C_{1-6}$ alkyl group.)

As a second aspect, the present invention relates to the polyester resin composition according to the first aspect, wherein $R^3$ and $R^4$ are a hydrogen atom.

As a third aspect, the present invention relates to the polyester resin composition according to the first or second aspect, wherein both $R^1$ and $R^2$ are —C(=O)$R^5$ (wherein each $R^5$ is independently a $C_{1-20}$ alkyl group or a phenyl group optionally substituted with a $C_{1-6}$; alkyl group).

As a fourth aspect, the present invention relates to the polyester resin composition according to the third aspect, wherein $R^5$ is a $C_{1-8}$ alkyl group.

As a fifth aspect, the present invention relates to the polyester resin composition according to the fourth aspect, wherein $R^5$ is an ethyl group or a propyl group.

As a sixth aspect, the present invention relates to the polyester resin composition according to any one of the first to fifth aspects, wherein the polyester resin is a polylactic acid) resin.

As a seventh aspect, the present invention relates to a polyester resin molded body obtained by crystallization of the polyester resin composition according to any one of the first to sixth aspects.

As an eight aspect, the present invention relates to a crystal nucleating agent including the 2-amino-1,3,5-triazine derivative according to any of the first to fifth aspects.

As a ninth aspect, the present invention relates to N,N'-(6-amino-1,3,5-triazine-2,4-diyl) dipropionamide of Formula [2].

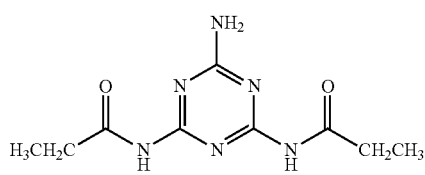

[2]

Effects of the Invention

In a polyester resin composition of the present invention, a specific 2-amino-1,3,5-triazine derivative is used as a crystal nucleating agent. For this reason, the polyester resin composition promotes an effect of promoting the crystallization of a polyester resin. Accordingly, a polyester resin composition having excellent heat resistance and molding processability can be provided.

In particular, as the polyester resin composition of the present invention, a polyester resin composition having extremely excellent transparency after crystallization can be provided as compared with a resin composition containing a conventional crystal nucleating agent.

BRIEF DESCRIPTION OF THE DRAWINGS

FIG. 1 is a diagram showing $^1$H NMR spectrum of N,N'-(6-amino-1,3,5-triazine-2,4-diyl) dipropionamide obtained in Example 1.

MODES FOR CARRYING OUT THE INVENTION

Hereinafter, the present invention will be described in detail.

The polyester resin composition of the present invention is a composition containing a polyester resin and a 2-amino-1,3,5-triazine derivative of Formula [1] (hereinafter also referred to as a derivative of Formula [1]).

[2-Amino-1,3,5-triazine derivative]

A 2-amino-1,3,5-triazine derivative used in the polyester resin composition of the present invention has a structure of Formula [1] described below.

The 2-amino-1,3,5-triazine derivative is suitably used as a crystal nucleating agent.

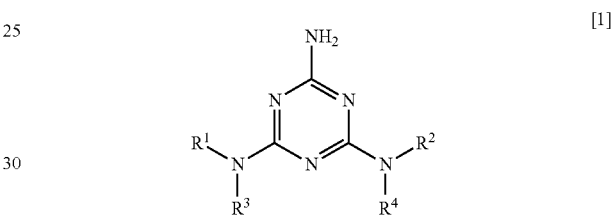

[1]

In the formula, each of $R^1$ and $R^2$ is independently —C(=O)$R^5$, —C(=O)O$R^6$, —C(=O)N$R^7R^8$, or —SO$_2R^9$, and each of $R^3$ and $R^4$ is independently a hydrogen atom, a $C_{1-6}$ alkyl group, —C(=O)$R^5$, —C(=O)O$R^6$, C(=O)N$R^7R^8$, or —SO$_2R^9$.

Each of $R^5$, $R^6$, and $R^9$ is independently a $C_{1-20}$ alkyl group or a phenyl group optionally substituted with a $C_{1-6}$ alkyl group, and each of $R^7$ and $R^8$ is independently a hydrogen atom, a $C_{1-20}$ alkyl group, or a phenyl group optionally substituted with a $C_{1-6}$ alkyl group.

The $C_{1-20}$ alkyl group may be any of linear, branched, and cyclic alkyl groups.

Examples of the linear alkyl groups include methyl group, ethyl group, n-propyl group, n-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-eicosyl group.

Examples of the branched alkyl groups include isopropyl group, isobutyl group, sec-butyl group, and tert-butyl group.

Examples of the cyclic alkyl groups include groups having a cyclopentyl ring structure and groups having a cyclohexyl ring structure.

Examples of the $C_{1-6}$ alkyl group include $C_{1-6}$ alkyl groups among the linear, branched, and cyclic alkyl groups.

Examples of the phenyl group optionally substituted with a $C_{1-6}$ alkyl group include phenyl group, p-tolyl group, 4-isopropylphenyl group, 4-butylphenyl group, and mesityl group.

In the 2-amino-1,3,5-triazine derivative of Formula [1], $R^3$ and $R^4$ are preferably a hydrogen atom.

In Formula [1], $R^1$ and $R^2$ are preferably —C(=O)$R^5$ ($R^5$ is the same as the definition described above), in which $R^5$ is preferably a $C_{1-8}$ alkyl group, and particularly preferably an ethyl group or a propyl group.

Particularly preferred examples thereof include N,N'-(6-amino-1,3,5-triazine-2,4-diyl) dipropionamide of Formula [2].

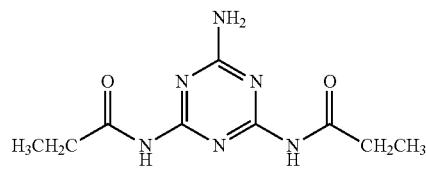

[2]

The polyester resin composition of the present invention may contain a 1,3,5-triazine derivative of Formula [3] described below as long as the effects of the present invention are not impaired.

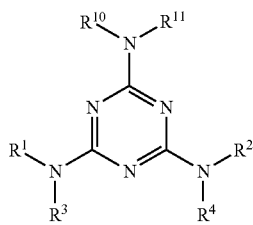

[3]

In the formula, $R^1$ to $R^4$ are the same as the definitions described in Formula [1].

$R^{10}$ is $-C(=O)R^5$, $-C(=O)OR^6$, $-C(=O)NR^7R^8$, or $-SO_2R^9$, and $R^{11}$ is a hydrogen atom, a $C_{1-6}$ alkyl group, $-C(=O)R^5$, $-C(=O)OR^6$, $C(=O)NR^7R^8$, or $-SO_2R^9$. $R^5$ to $R^9$ are the same as the definitions described in Formula [1].

A method for producing the amino-1,3,5-triazine derivative of Formula [1] is not particularly limited. The 2-amino-1,3,5-triazine derivative of Formula [1] can be easily obtained, for example, by an amidation reaction, an urethane-forming reaction, a carbamide-forming reaction, or a sulfonamide-forming reaction of melamines with carboxylic acid or an active body thereof (acid halide, acid anhydride, acid azide, active ester, etc.), a halogenated formic acid ester, isocyanate, or sulfonic acid or an active body thereof (sulfonic acid halide, sulfonic anhydride, etc.), in accordance with a conventionally known method.

Specifically, the 2-amino-1,3,5-triazine derivative can be produced by schemes of Formulae [4] to [7].

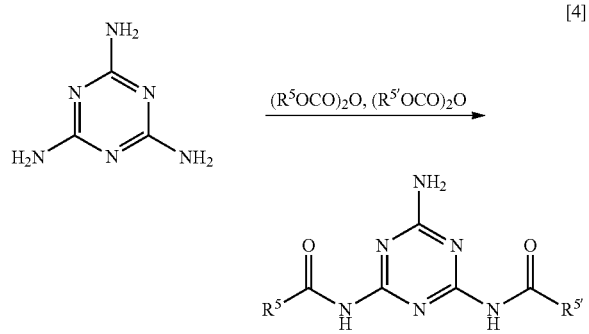

[4]

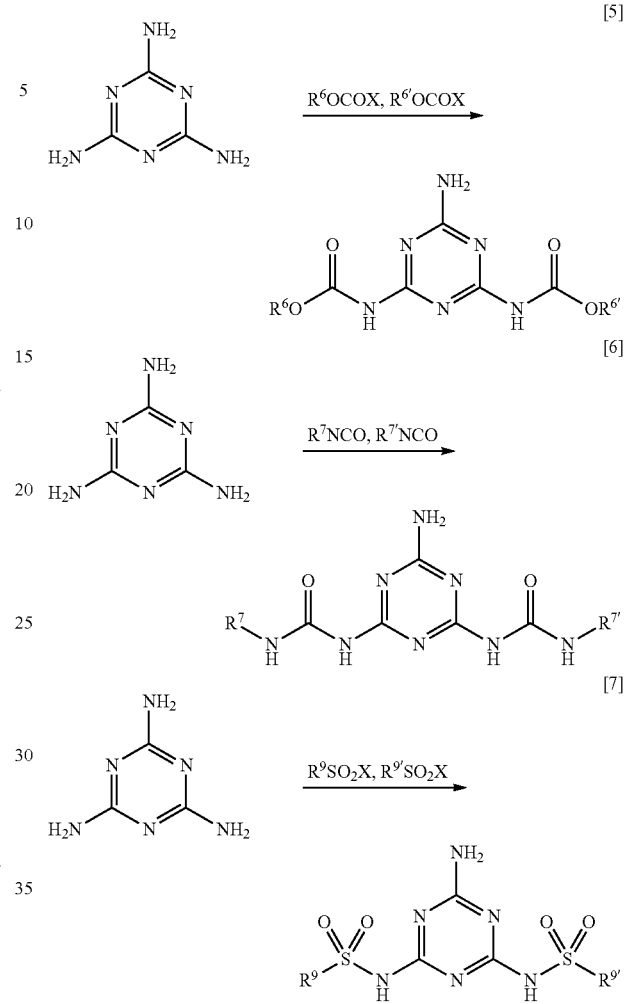

In Formulae [4] to [7], $R^5$ to $R^7$, and $R^9$ have the same meanings as described above, $R^{5'}$ and $R^5$, $R^{6'}$ and $R^6$, $R^{7'}$ and $R^7$, and $R^{9'}$ and $R^9$ have the same meaning to each other. Each of them may be the same group or different groups. X is not particularly limited as long as it is a group capable of producing a desired bond (amide bond or sulfonamide bond), and examples thereof include a halogen atom such as a chlorine atom and a bromine atom. When $R^{5'}$ and $R^5$, $R^{6'}$ and $R^6$, $R^{7'}$ and $R^7$, and $R^{9'}$ and $R^9$ are different groups, each one of them may be first reacted, and the other one of them may be then reacted, or both of them may be simultaneously reacted.

[Polyester Resin]

Examples of the polyester resin used in the present invention include poly(hydroxyalkanoic acid) (PHA) such as poly(glycolic acid) (PGA), poly(lactic acid) (PLA), poly(3-hydroxybutyrate) (PHB), poly((3-hydroxybutyrate)-co-(3-hydroxyvalerate)) (PHBV), poly((3-hydroxybutyrate)-co-(3-hydroxyhexanoate)) (PHBH), and poly((3-hydroxybutyrate)-co-(4-hydroxybutyrate)) (P3/4HB); polycondensates of diol and dicarboxylic acid such as poly(ethylene naphthalate) (PEN), poly(ethylene succinate), poly(ethylene succinate/adipate), poly(ethylene terephthalate) (PET), poly(butylene adipate/terephthalate), poly(butylene naphthalate), poly(butylene succinate) (PBS), poly(butylene succinate/adipate), poly(butylene succinate/ carbonate), and poly(butylene terephthalate) (PBT); and polycaprolactone. The polyester resins may be used singly or in combinations of two or more of them.

Among these, a poly(lactic acid) resin is preferred.

<Poly(Lactic Acid) Resin>

The poly(lactic acid) resin may contain a homopolymer or a copolymer of poly(lactic acid). When the poly(lactic acid) resin is a copolymer, the arrangement style of the copolymer may be any of a random copolymer, an alternating copolymer, a block copolymer, and a graft copolymer.

In addition, the poly(lactic acid) resin may be a blended polymer containing a homopolymer or a copolymer of poly(lactic acid) as a main component with another resin. Examples of the other resin include a biodegradable resin other than a poly(lactic acid) resin described below, a universally applicable thermoplastic resin, and a universally applicable thermoplastic engineering plastic.

The poly(lactic acid) is not particularly limited, and examples thereof include poly(lactic acid) obtained by ring-opening polymerization of lactide, and poly(lactic acid) obtained by direct polycondensation of D-form, L-form, or racemate of lactic acid. Examples thereof also include poly(L-lactic acid) (VELA), poly(D-lactic acid) (MLA), and stereo complexes thereof. The poly(lactic acid) generally has the number average molecular weight of about 10,000 to about 500,000. A poly(lactic acid) resin cross-linked with a crosslinker using heat, light, radiation, or the like can be used.

Examples of the biodegradable resin other than a poly (lactic acid) resin usable as the blended polymer include poly(hydroxyalkanoic acid) (PHA) such as poly(glycolic acid) (PGA), poly(3-hydroxybutyrate) (PIM), poly((3-hydroxybutyrate)-co-(3-hydroxyvalerate)) (PHBV), poly((3-hydroxybutyrate)-co-(3-hydroxyhexanoate)) (PHBH), and poly((3-hydroxybutyrate)-co-(4-hydroxybutyrate)) (P3/4HB); polycondensates of diol and aliphatic dicarboxylic acid such as poly(butylene succinate) (PBS), poly(butylene succinate/adipate), poly(butylene succinate/carbonate), poly(butylene adipate/terephthalate), poly(ethylene succinate), and poly(ethylene succinate/adipate); polycaprolactone; poly(vinyl alcohol); modified starch; cellulose acetate; chitin and chitosan; and lignin.

Examples of the universally applicable thermoplastic resin usable as the blended polymer include a polyolefin resin such as polyethylene (PE), a polyethylene copolymer, polypropylene (PP), a polypropylene copolymer, polybutylene (PB), an ethylene-vinyl acetate copolymer (EVA), an ethylene-ethyl acrylate copolymer (EEA), and poly(4-methyl-1-pentene); a polystyrenic resin such as polystyrene (PS), high-impact polystyrene (HIPS), an acrylonitrile-styrene copolymer (AS), and an acrylonitrile-butadiene-styrene copolymer (ABS); a polyvinyl chloride) resin; a polyurethane resin; a phenolic resin; an epoxy resin; an amino resin; and an unsaturated polyester resin.

Examples of the universally applicable engineering plastic include a polyamide resin; a polyimide resin; a polycarbonate resin; a poly(phenylene ether) resin; a modified poly(phenylene ether) resin; a polyester resin such as poly(ethylene terephthalate) (PET) and poly(butylene terephthalate) (PBT); a polyacetal resin; a polysulfone resin; and a poly(phenylene sulfide) resin.

[Resin Composition]

The polyester resin composition of the present invention contains the 2-amino-1,3,5-triazine derivative of Formula [1] in an amount of 0.01 to 10 parts by mass relative to 100 parts by mass of the polyester resin. When the amount of the 2-amino-1,3,5-triazine derivative to be added is 0.01 parts by mass or more, sufficient crystallization rate can be achieved. However, even when the amount is more than 10 parts by mass, the crystallization rate is not further improved. Therefore, it is economically advantageous to use the 2-amino-1,3,5-triazine derivative in an amount of 10 parts by mass or less.

It is preferable that the polyester resin composition contain the derivative of Formula [1] in an amount of 0.1 to 5 parts by mass, and more preferably 0.1 to 2 parts by mass relative to 100 parts by mass of the polyester resin.

When the polyester resin composition of the present invention contains the 1,3,5-triazine derivative of Formula [3], it is preferable that the 1,3,5-triazine derivative be contained in an amount of about 0.5 parts by mass or less relative to 100 parts by mass of the polyester resin.

In the present invention, a method of adding the derivative of Formula [1] to the polyester resin is not particularly limited, and can be carried out by a known method. For example, the polyester resin, the derivative of Formula [1], and various additives described below may be individually mixed in several mixers, and kneaded with a single- or double-screw extruder, or the like. The mixture is generally kneaded at a temperature of about 150 to about 220° C. Another process can be also carried out in which a master batch containing each component in a high concentration is produced and added to the polyester resin. Further, the derivative of Formula [1] can be added in a polymerization step of the polyester resin.

For the polyester resin composition of the present invention, a known inorganic filler may be used. Examples of the inorganic filler include glass fibers, carbon fibers, talc, mica, silica, kaolin, clay, wollastonite, glass beads, glass flakes, potassium titanate, calcium carbonate, magnesium sulfate, and titanium oxide. The form of these inorganic fillers may be any of fibers, grains, plates, needles, spheres, and powders. The inorganic filler can be used in an amount of 300 parts by mass or less relative to 100 parts by mass of the polyester resin.

For the polyester resin composition of the present invention, a known flame retardant may be used. Examples of the flame retardant include a halogen-based flame retardant such as a bromine-based flame retardant and a chlorine-based flame retardant; an antimony-based flame retardant such as antimony trioxide and antimony pentoxide; inorganic flame retardant such as aluminum hydroxide, magnesium hydroxide, and a silicone-based compound; a phosphorus-based flame retardant such as red phosphorus, phosphate esters, ammonium polyphosphate, and phosphazene; a melamine-based flame retardant such as melamine, melam, melem, melon, melamine cyanurate, melamine phosphate, melamine pyrophosphate, melamine polyphosphate, a melamine-melam-melem polyphosphate double salt, melamine alkylphosphonate, melamine phenylphosphonate, melamine sulfate, and melam methanesufonate; and a fluorine-based resin such as polytetrafluoroethylene (PTFE). The flame retardants can be used in an amount of 200 parts by mass or less relative to 100 parts by mass of the polyester resin.

In addition to the components, various additives that are usually used in production of a general synthetic resin such as a thermal stabilizer, a photostabilizer, an ultraviolet absorber, an antioxidant, an impact modifier, an antistatic agent, a pigment, a colorant, a release agent, a lubricant, a plasticizer, a compatibilizer, a foaming agent, a flavor, an antibacterial antifungal agent, various types of coupling agents such as a silane-based coupling agent, a titanium-based coupling agent, and an aluminum-based coupling agent, other various fillers, and other crystal nucleating agents can be used in combination.

[Resin Molded Body]

The present invention also relates to a polyester resin molded body obtained by crystallization of the polyester resin composition.

When the polyester resin composition of the present invention is applied to a common molding method such as general injection molding, blow molding, vacuum molding, compression molding, and extrusion, various molded bodies can be easily produced.

The polyester resin molded body of the present invention includes the crystallized polyester resin and a crystal nucleating agent including the 2-amino-1,3,5-triazine derivative of Formula [1].

The polyester resin molded body of the present invention can be obtained by use of the polyester resin composition of the present invention and crystallization of a polyester resin contained therein. A method of crystallizing a polyester resin is not particularly limited, and for example, a polyester resin composition may be heated at a temperature equal to or higher than a temperature capable of causing crystallization during a molding process in which the polyester resin composition is formed into a specific shape. In the process, the polyester resin composition is heated and molded at a temperature equal to or higher than the melting point, and quenched to form a molded body in an amorphous state, and the molded body is heated (annealed). Thus, crystallization can be carried out.

In general, a temperature for crystallization of a polyester resin is appropriately selected from a temperature ranging from the glass transition temperature or more of the resin to less than the melting point. For example, a poly(lactic acid) resin is used as a polyester resin, the heating (annealing) temperature is 60 to 170° C., preferably 70 to 130° C., and more preferably 80 to 120° C. At a heating (annealing) temperature of 60° C. or higher, crystallization is promoted for a more practical time. At a heating (annealing) temperature of 170° C. or lower, a molded body in which a larger number of spherulites with small crystal diameter exist, that is, transparency is excellent is obtained.

Since the crystal diameters of the polyester resin molded body of the present invention are small and similar to each other, the polyester resin molded body has excellent transparency, heat resistance, and mechanical strength.

EXAMPLES

Hereinafter, the present invention will be described more specifically with reference to Examples, but the present invention is not limited to the following description.

In Examples, apparatuses and conditions used for preparation of samples and analysis of physical properties are as follows.

(1) $^1$H NMR spectrum
Apparatus: JNM-ECX300 manufactured by JEOL Ltd.
Solvent: DMSO-$d_6$((CD$_3$)$_2$SO))
Base peak: DMSO-$d_6$ (2.49 ppm)
(2) Measurement of melting point/sublimation point and measurement of 5% weight-decrease temperature (Td$_{5\%}$)
Apparatus: Thermo plus EVO II TG8120 manufactured by Rigaku Corporation
Measurement condition: in air atmosphere
Temperature increasing rate: 10° C./min (30 to 500° C.)
(3) Melt-kneading
Apparatus A: LABO PLASTOMILL μ KF6V manufactured by Toyo Seiki Seisaku-Sho, Ltd.
Apparatus B (extruder): same-direction rotating biaxial extruder HK-25D (41 D) (screw diameter: 25 mm, L/D-41) manufactured by PARKER CORPORATION
Apparatus B (metering apparatus): Vibratory compact weight feeder K-CL-24-KV1 manufactured by K-Tron
(4) Hot press
Apparatus: SA-302 Tabletop Teat Press manufactured by TESTER SANGYO CO., LTD.
(5) Extrusion (T-die method)
Apparatus: T-die extruder manufactured by SOUKEN Co., Ltd.
T-die: dice width 300 mm, lip width 0.5 mm (coat hanger die)
Extruder: caliber φ30, L/D=38, CR 2.75 (full flight screw)
(6) Differential Scanning calorimetry (DSC)
Apparatus: Diamond DSC manufactured by PerkinElmer Japan Co., Ltd.
(7) Haze Measurement
Apparatus: Haze meter NDH 5000 manufactured by NIPPON DENSHOKU INDUSTRIES CO., LTD.

Example 1

Production of N,N'-(6-amino-1,3,5-triazine-2,4-diyl) dipropionamide (Compound 1)

1.26 g (10 mmol) of melamine [manufactured by NISSAN CHEMICAL INDUSTRIES, LTD.] and 50 g of pyridine were placed in a reaction flask equipped with a stirrer and stirred. 2.86 g (22 mmol) of propionic anhydride [manufactured by KANTO CHEMICAL CO., INC] was added to the flask, and the mixture was heated and refluxed at a liquid temperature of 110° C. for 4 hours. The reaction liquid was cooled to room temperature (about 25° C.), the precipitate was then collected by filtration, and washed with 50 g of methanol three times, and with 50 g of acetone three times. The resulting wet product was dried under reduced pressure at 80° C. for 8 hours to obtain 1.64 g of target Compound 1 as a white powder (yield: 69%). FIG. 1 shows $^1$H NNR spectrum of Compound 1.

$^1$H NNR (DMSO-$d_6$): δ 9.92 (s, 2H), 7.14 (s, 2H), 2.62 (q, J=7.4 Hz, 4H), 1.00 (t, J=7.4 Hz, 6H) (ppm)
Sublimation point: 272.6° C., Td$_{5\%}$: 255.2° C.

Production Example 1

Production of N,N''-(6-amino-1,3,5-triazine-2,4-diyl) dibutylamide (Compound 2)

1.76 g of target Compound 2 (yield: 66%) was obtained as a white powder by the same operation as in Example 1 except that 3.48 g (22 mmol) of butyric anhydride was used instead of propionic anhydride.
Sublimation point: 277.4° C., Td$_{5\%}$: 248.5° C.

Production Example 2

Production of N,N'-(6-amino-1,3,5-triazine-2,4-diyl) dihexanamide (Compound 3)

0.90 g of target Compound 3 (yield: 25%) was obtained as a white powder by the same operation as in Example 1 except that 4.71 g (22 mmol) of capronic anhydride was used instead of propionic anhydride.

Sublimation point: 244.3° C., Td$_{5\%}$: 257.2° C.

Production Example 3

Production of N,N'-(6-amino-1,3,5-triazine-2,4-diyl) dioctanamide (Compound 4)

1.97 g of target Compound 4 (yield: 52%) was obtained as a white powder by the same operation as in Example 1 except that 5.95 g (22 mmol) of caprylic anhydride was used instead of propionic anhydride.
Sublimation point: 227.7° C., Td$_{5\%}$: 248.9° C.

Reference Example 1

Production of N,N'-(1,3,5-triazine-2,4-diyl) dipropionamide (Compound 5)

1.11 g (10 mmol) of 2,4-diamino-1,3,5-triazine [manufactured by Tokyo Chemical Industry Co., Ltd.] and 30 g (0.23 mol) of propionic anhydride [manufactured by KANTO CHEMICAL CO., INC.] were placed in a reaction flask equipped with a stirrer and stirred at a liquid temperature of 130° C. for 3 hours. The reaction liquid was cooled to room temperature (about 25° C.), the precipitate was then collected by filtration, and washed with 30 g of methanol three times, and with 30 g of acetone three times. The resulting wet product was dried under reduced pressure at 80° C. for 8 hours to obtain 2.13 g of target Compound 5 as a white powder (yield: 95%).
Sublimation point: 279.9° C., Td$_{5\%}$: 239.7° C.

Reference Example 2

Production of N,N'-(6-methyl-1,3,5-triazine-2,4-diyl) dipropionamide (Compound 6)

136 g of target Compound 6 (yield: 56%) was obtained as a white powder by the same operation as in Reference Example 1 except that 1.25 g (10 mmol) of 2,4-diamino-6-methyl-1,3,5-triazine [manufactured by Tokyo Chemical Industry Co., Ltd.] was used instead of 2,4-diamino-1,3,5-triazine.
Sublimation point: 221.0° C., Td$_{5\%}$: 212.1° C.

Reference Example 3

Production of N,N'-(6-phenyl-1,3,5-thiazine-2,4-diyl) dipropionamide (Compound 7)

2.09 g of target Compound 7 (yield: 70%) was obtained as a white powder by the same operation as in Reference Example 1 except that 1.87 g (10 mmol) of benzoguanamine [manufactured by Tokyo Chemical Industry Co., Ltd.] was used instead of 2,4-diamino-1,3,5-tribune.
Sublimation point: 224.1° C., Td$_{5\%}$: 267.8° C.

Reference Example 4

Production of N,N'-(6-dimethylamino-1,3,5-triazine-2,4-diyl) dipropionamide (Compound 8)

1.32 g of target Compound 8 (yield: 50%) was obtained as a white powder by the same operation as in Reference Example 1 except that 1.54 g (10 mmol) of 2,4-diamino-6-dimethylamino-1,3,5-triazine [manufactured by Tokyo Chemical Industry Co., Ltd.] was used instead of 2,4-diamino-1,3,5-triazine.
Melting point: 212.1° C., Td$_{5\%}$: 233.3° C.

Reference Example 5

Production of N,N',N''-(1,3,5-triazine-2,4,6-triyl) tripropionamide (Compound 9)

2.50 g of target Compound 9 (yield: 85%) was obtained as a white powder by the same operation as in Reference Example 1 except that 1.26 g (10 mmol) of melamine [manufactured by NISSAN CHEMICAL INDUSTRIES, LTD.] was used instead of 2,4-diamino-1,3,5-triazine.
Sublimation point: 284.9° C., Td$_{5\%}$: 263.8° C.

Reference Example 6

Production of $N^1,N^3,N^5$-tricyclohexylbenzene-1,3,5-tricarboxamide (Compound 10)

4.96 g (50 mmol) of cyclohexylamine [manufactured by Tokyo Chemical Industry Co., Ltd.], 3.04 g (30 mmol) of triethylamine [manufactured by Tokyo Chemical Industry Co., Ltd.], and 87 g of toluene were placed in a reaction flask equipped with a stirrer. While the solution was stirred in an ice bath, a solution of 2.65 g (10 mmol) of trimesic acid chloride [manufactured by Hangzhou Volant Technology Co., Ltd,] dissolved in 87 g of toluene was added dropwise. After completion of dropwise addition, the temperature was slowly increased to room temperature (about 25° C.) and the mixture was stirred as it was for 16 hours. Toluene was removed using an evaporator, the residue was dissolved in 280 g of N,N-dimethylformamide (DMF), and 500 g of methanol and 300 g of water were added to the mixture. The precipitated solid was collected by filtration and washed with 2.40 g of methanol. The resulting wet product was dried under reduced pressure at 80° C. for 8 hours to obtain 2.65 g of target Compound 10 as a white powder (yield: 58%).
Melting point: not observed (decomposition), Td$_{5\%}$: 318.6° C.

Examples 2 to 5 and Comparative Examples 1 to 6

0.5 parts by mass of each of Compounds 1 to 10 described in Table 1 as a crystal nucleating agent was added to 100 parts by mass of polylactic acid) resin [Ingeo Biopolymer 300ID, injection grade, manufactured by NatureWorks LLC], and the mixture was melted and kneaded at 185° C. and 50 rpm for 5 minutes (using Apparatus A) to obtain a poly(lactic acid) resin composition.
The resin composition and a polyimide film (spacer) having a thickness of 130 μm was placed between two brass plates with 1.80 mm×120 mm×2 mm, and hot pressed at 200° C. and 25 kgf/cm$^2$ for 1 minute. Immediately after the hot pressing, the film-shaped resin composition was taken off from the space between the brass plates, placed between other brass plates (with the same size as the above-described brass plates) of about room temperature (about 25° C.), and quenched. As a result, an amorphous film-shaped molded body of poly(lactic acid) resin containing the crystal nucleating agent was obtained.
5 mg of the amorphous film-shaped molded body was cut out, and the crystallization behavior was evaluated using DSC. In the evaluation, the time taken from when the temperature increases to 110° C. during heating at 500°

C./min and is maintained at 110° C. to when heat generation (enthalpy of crystallization ΔHc) due to crystallization of poly(lactic acid) reaches a peak was measured as a half crystallization time ($t_{1/2}$). A smaller value of $t_{1/2}$ represents a faster crystallization rate under the same condition and a more excellent effect as the crystal nucleating agent. Table 1 shows the results.

The amorphous film-shaped molded body was cut out into a rectangle of 40 mm×25 mm. The film-shaped molded body was annealed on a hot plate of 110° C. for 30 minutes to obtain a crystallized film-shaped molded body of poly(lactic acid) resin (thickness: about 130 μm).

The transparency of the obtained crystallized film-shaped molded body was evaluated. In the evaluation, the haze of the film-shaped molded body was measured at three different points, and an average value thereof was calculated. Table 1 shows the results. A lower haze represents higher transparency.

5 mg of the crystallized film-shaped molded body was cut out, and the crystallinity was evaluated using DSC. In the evaluation, the enthalpy of crystallization ΔHc and the crystal melting enthalpy ΔHm at which the temperature was increased at 10° C./min to 200° C. were measured, and a value obtained by calculating (ΔHm−ΔHc)/ΔH$_0$×100 was used as a crystallinity. Table 1 shows the results. Herein, ΔH$_0$ represents a perfect ideal crystal melting enthalpy, and as a value of poly(lactic acid) (α crystal), 93 J/g was used.

Example 6

The same operation and evaluation as in Example 2 were carried out except that [Ingeo Biopolymer 4032D], extrusion grade, manufactured by NatureWorks LLC] was used as a poly(lactic acid) resin, and the measurement temperature of $t_{1/2}$ and the annealing temperature were each changed into 90° C. Table 1 shows the results.

Comparative Example 7

A poly(lactic acid) resin composition was obtained in the same manner as in Example 2 except that a crystal nucleating agent was not added, and the operation and evaluation were then carried out similarly. Table 1 shows the results.

TABLE 1

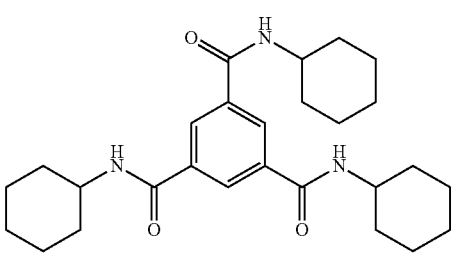 [SMILES: O=C(NC1CCCCC1)c1cc(C(=O)NC2CCCCC2)cc(C(=O)NC2CCCCC2)c1]

| | Crystal nucleating agent | R | $R^1, R^2$ | $t_{1/2}$ [min] | Haze | Crystallinity |
|---|---|---|---|---|---|---|
| Example 2 | Compound 1 | —NH$_2$ | —CH$_2$CH$_3$ | 0.43 | 7.0 | 37.7 |
| Example 6 | Compound 1 | —NH$_2$ | —CH$_2$CH$_3$ | 0.43 | 3.6 | 36.0 |
| Example 3 | Compound 2 | —NH$_2$ | —(CH$_2$)$_2$CH$_3$ | 0.40 | 8.7 | 38.4 |
| Example 4 | Compound 3 | —NH$_2$ | —(CH$_2$)$_4$CH$_3$ | 0.83 | 40.1 | 36.0 |
| Example 5 | Compound 4 | —NH$_2$ | —(CH$_2$)$_6$CH$_3$ | 0.35 | 29.8 | 33.2 |
| Comparative Example 1 | Compound 5 | —H | —CH$_2$CH$_3$ | 1.11 | 67.9 | 32.0 |
| Comparative Example 2 | Compound 6 | —CH$_3$ | —CH$_2$CH$_3$ | 1.27 | 64.9 | 32.6 |
| Comparative Example 3 | Compound 7 | —C$_6$H$_5$ | —CH$_2$CH$_3$ | 1.41 | 69.9 | 38.1 |
| Comparative Example 4 | Compound 8 | —N(CH$_3$)$_2$ | —CH$_2$CH$_3$ | 1.13 | 73.0 | 29.4 |
| Comparative Example 5 | Compound 9 | —NHCOCH$_2$CH$_3$ | —CH$_2$CH$_3$ | 1.10 | 42.3 | 34.2 |
| Comparative Example 6 | Compound 10 | | | 1.05 | 65.2 | 34.6 |
| Comparative Example 7 | None | — | | 1.38 | 78.8 | 37.9 |

The resin compositions in Examples 2 to 6 in which each of Compounds 1 to 4 as a 2-amino-1,3,5-triazine derivative was added, as shown in Table 1, have results in which the half crystallization time ($t_{1/2}$ is short and the transparency after crystallization is excellent.

In contrast, in Comparative Example 1 using a triazine derivative not substituted with an amino group (Compound 5), Comparative Examples 2 to 5 using each of triazine derivatives substituted with a substituent other than an amino group (Compounds 6 to 9), Comparative Example 6 using Compound 10 in which the bonding order of amido groups to be bonded to an aromatic ring as a known crystal nucleating agent for poly(lactic acid) was different, and Comparative Example 7 in which a crystal nucleating agent was not contained, the half crystallization time ($t_{1/2}$) was 1 minute or more, that is, the crystallization rate was low, and the transparency after crystallization was low.

Example 7

0.5 parts by mass of Compound 1 as a crystal nucleating agent was added to 100 parts by mass of poly(lactic acid) resin [Ingeo Biopolymer 4032D, extrusion grade, manufactured by NatureWorks LLC], and the mixture was melted and kneaded at 170 to 180° C. and 150 rpm (using Apparatus B) to obtain poly(lactic acid) resin pellets.

The pellets were extruded into a sheet using a T-die extruder from a T-die at a melting resin temperature of 200° C. (drawing rate: 0.4 m/min), quenched by a first roller (at a roller temperature of 56.5° C.), and then annealed by a second roller (at a roller temperature of 88° C.) to obtain a crystalline poly(lactic acid) resin sheet with a thickness of about 200 μm. A contact time of the sheet with the second roller was 36 seconds.

The transparency and the crystallinity of the obtained sheet were evaluated by the same procedure as in Example 2. The haze value was 2.3% and the crystallinity was 35.5%.

As shown in Examples 2 to 6 and Example 7, a molded body having excellent transparency after crystallization can be obtained without depending on a method for molding (crystallizing) the polyester resin composition of the present invention.

The invention claimed is:

1. A polyester resin composition containing 100 parts by mass of a polyester resin and 0.01 to 2 parts by mass of a 2-amino-1,3,5-triazine derivative of Formula [1]:

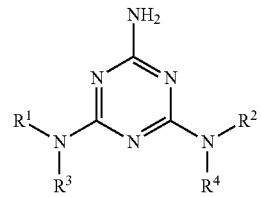

where:
both of $R^1$ and $R^2$ are —C(=O)$R^{10}$,
each $R^{10}$ is a $C_{1-20}$ alkyl group,
each of $R^3$ and $R^4$ is independently a hydrogen atom, a $C_{1-6}$ alkyl group, —C(=O)$R^5$, —C(=O)O$R^6$, C(=O)N$R^7R^8$, or —SO$_2R^9$,
each of $R^5$, $R^6$, and $R^9$ is independently a $C_{1-20}$ alkyl group or a phenyl group optionally substituted with a $C_{1-6}$ alkyl group, and
each of $R^7$ and $R^8$ is independently a hydrogen atom, a $C_{1-20}$ alkyl group, or a phenyl group optionally substituted with a $C_{1-6}$ alkyl group.

2. The polyester resin composition according to claim 1, wherein $R^3$ and $R^4$ are a hydrogen atom.

3. The polyester resin composition according to claim 1, wherein $R^{10}$ is a $C_{1-8}$ alkyl group.

4. The polyester resin composition according to claim 3, wherein $R^{10}$ is an ethyl group or a propyl group.

5. The polyester resin composition according to claim 1, wherein the polyester resin is a poly(lactic acid) resin.

6. A polyester resin molded body obtained by crystallization of the polyester resin composition according to claim 1.

7. The polyester resin composition according to claim 2, wherein the polyester resin is a poly(lactic acid) resin.

* * * * *